(12) United States Patent
Stokes

(10) Patent No.: US 6,366,819 B1
(45) Date of Patent: Apr. 2, 2002

(54) BIOSTABLE SMALL FRENCH LEAD

(75) Inventor: Kenneth B. Stokes, Anoka, MN (US)

(73) Assignee: Medtronic, Inc.

( * ) Notice: Subject to any disclaimer, the term of this patent is extended or adjusted under 35 U.S.C. 154(b) by 0 days.

(21) Appl. No.: 09/677,914

(22) Filed: Oct. 3, 2000

(51) Int. Cl.[7] ................................................. A61N 1/05
(52) U.S. Cl. ...................................................... 607/119
(58) Field of Search ................................. 607/115–156; 600/372–385

(56) References Cited

U.S. PATENT DOCUMENTS

| | | |
|---|---|---|
| 5,246,014 A | 9/1993 | Williams et al. |
| 5,282,844 A | 2/1994 | Stokes et al. |
| 5,342,414 A | 8/1994 | Mehra |
| 5,375,609 A * | 12/1994 | Molacek et al. |
| 5,741,331 A * | 4/1998 | Pinchuk |
| 5,845,396 A | 12/1998 | Altman et al. |
| 5,871,530 A | 2/1999 | Williams et al. |
| 5,986,034 A * | 11/1999 | DiDomenico et al. |

* cited by examiner

*Primary Examiner*—Scott M. Getzow
(74) *Attorney, Agent, or Firm*—Beth L. McMahon

(57) ABSTRACT

A medical lead having a diameter of no greater than 3 French and employing an insulation material that is substantially stiffer than would normally be employed in the context of a permanently implantable cardiac pacing lead is disclosed. A material having a Young's modulus of at least 25,000 pounds per square inch such as Pellethane 2363-75D, or an even stiffer polymer, is used to provide a lead body that does not exhibit a whip-like effect in response to such movement as would occur during a heart beat. In order to prevent the increased stiffness of the lead body from increasing the possibility that the distal lead tip will perforate the heart tissue, the lead is provided with a distal surface that is not reduced in size. This surface reduces the pressure exerted by the distal lead tip upon body tissue to no greater than 3.6 pounds per square inch. The distal tip may carry an electrode of the same or substantially smaller surface area, allowing the lead to retain desirable electrical characteristics for sensing of cardiac depolarizations and delivery of cardiac pacing pulses.

10 Claims, 3 Drawing Sheets

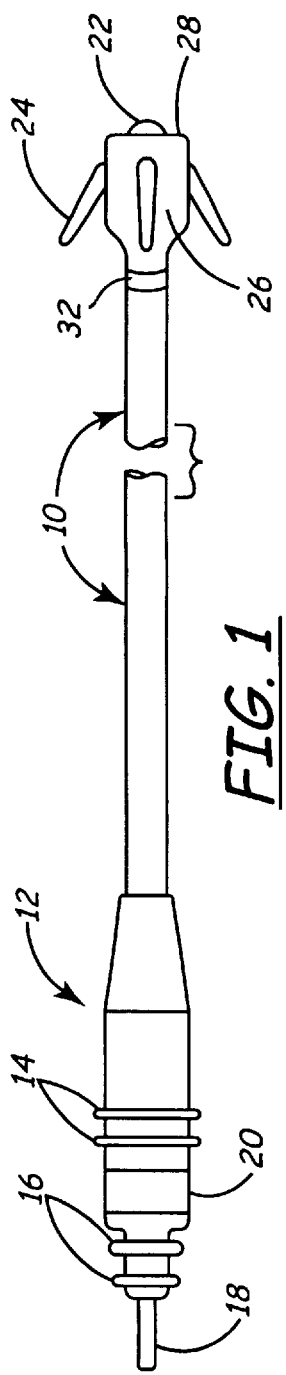
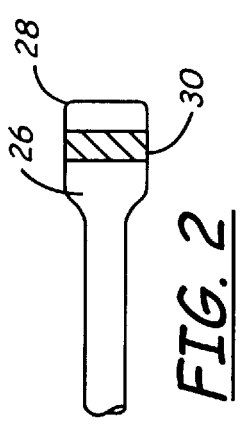
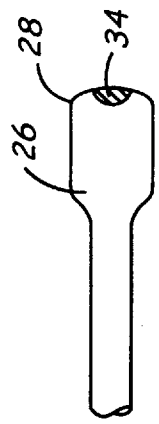
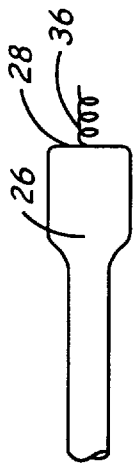
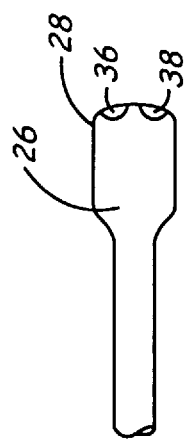

BIOSTABLE SMALL FRENCH LEAD

BACKGROUND OF THE INVENTION

The present invention relates generally to implantable cardiac leads, and more particularly to endocardial leads having small diameter lead bodies.

Over the past few years, there has been a substantial effort to reduce the diameter of endocardial pacing, cardioversion and defibrillation leads. Reduction in lead body diameter facilitates placement of multiple leads through a single blood vessel and also minimizes interference between the lead body and the tricuspid valve, in the case of leads implanted in the right ventricle. In addition, a reduction in lead body size has generally been accompanied by a reduction in the lead body's flexural stiffness or bending moment. This reduction in lead body flexural stiffness has generally been seen as an advantage, in that it reduces the possibility of perforation of heart tissue by the distal tip of the lead.

Some of the considerations underlying the quest for leads of ever-decreasing size and flexural stiffness are discussed in U.S. Pat. No. 5,246,014 issued to Williams et al, which discloses a lead having a diameter in the 1–2 French range. Small diameter defibrillation leads are disclosed in U.S. Pat. No. 5,871,530, also issued to Williams et al.

SUMMARY OF THE INVENTION

While small diameter pacing leads with highly flexible lead bodies do reduce the possibility of perforation and do facilitate the passage of multiple leads through the same blood vessel, e.g., the cephalic or subclavian vein, it has been determined that very small diameter and very flexible leads tend to cause substantial damage within the heart, due to their tendency to be rapidly moved within the heart chamber in a "whip-like" fashion. This damage may result in the formation of substantially more coliform vegetations (fibrous nodules) on the heart wall and valve leaflets than would be caused by stiffer leads.

The leads of the present invention retain the advantages of a small diameter lead body while avoiding damage due to whip-like movement of the lead body within the heart chamber. The present invention accomplishes this result by means of a lead body employing an insulation material that has a substantially higher Young's modulus (tensile stiffness) than would normally be employed in the context of a permanently implantable cardiac pacing lead.

The properties of the inventive lead structure may be considered using the principal that the flexural stiffness, or bending moment, of a fiber or tube varies with the tensile modulus, and the diameter to the $4^{th}$ power. That is, for a tube, the bending moment, or flexural stiffness is determined as:

$$(\text{Young's modulus}) \times (OD^4 - ID^4)/64$$

wherein OD and ID represent the Outer and Inner Diameters, respectively, of the tube, and Young's modulus is a measure of tensile stiffness of the material employed to manufacture the tube.

According to the current invention, a very stiff and even brittle material such as glass or carbon can be used to make flexible fabrics by using them in the form of very fine fibers. Such materials may provide a lead body which has a bending moment approximating that of prior art large diameter leads, while retaining the desired small diameter lead body. Because the bending moment of the leads of the current invention remains relatively unchanged, the possibility of perforation of the heart tissue by the distal tip of the passively fixed (tined) lead body using conventional electrode assemblies is not increased. The pressure that can be applied to the endocardium by the distal tip, as measured in pounds per square inch, is therefore similar to that of presently implanted larger leads. Alternatively, the distal tip may be a corkscrew which, when inserted within the cardiac tissue, prevents perforation. The electrode typically has a surface area of about 1.5 to 6 mm$^2$, allowing the lead to retain desirable electrical characteristics for sensing of cardiac depolarizations and delivery of cardiac pacing pulses.

In one embodiment, the outer diameter of the current lead is smaller than 3.0 French, and may be as small as 1.0 French. The lead body insulation is formed of Pellethane 2363-55D, 75D, or an even stiffer polymer, such as Genymere polyimide (Virginia Power Nuclear Services Company). The material selection may depend upon the tubing diameters required. In the context of a larger diameter pacing lead, including bipolar coaxial leads wherein two tubings are required, such materials would generally provide leads far too rigid for permanent implant, risking perforation of the myocardium and possible tamponade which can be lethal. In the context of a lead having an outer diameter of 3 French or less, however, the minimal cross-sectional diameters of the insulation produces a lead body having overall bending moment characteristics similar to prior art, larger diameter leads employing silicone rubber or softer polyurethanes as insulative materials.

According to one aspect of the invention, the distal end of the lead body may be designed to present a cross-sectional area similar to that provided by prior art larger diameter leads of similar lead body bending moment. A similar surface area pacing electrode may be located in this tip. The pacing electrode may be, for example, a porous sintered electrode with the capability of eluting a glucocorticosteroid such as dexamethasone or beclamethasone, similar to those described in U.S. Pat. No. 5,282,844 issued to Stokes et al and incorporated herein by reference in its entirety. Alternatively, the pacing/sensing electrode might be arranged as a "ring tip" electrode, extending around the external periphery of the distal portion of the lead body, resembling the electrode disclosed in U.S. Pat. No. 5,342,414 issued to Mehra, also incorporated herein by reference in its entirety. Other electrode configurations, including the use of multiple small electrodes disbursed across the distal tip surface of the lead body and/or active fixation electrodes may also be substituted.

BRIEF DESCRIPTION OF THE DRAWINGS

FIG. 1 is a plan view of a lead according to the present invention.

FIG. 2 is a cutaway view through the distal portion of the lead of FIG. 1.

FIG. 3 is a plan view of electrode head assembly incorporating an embedded electrode.

FIG. 4 is a plan view of electrode head incorporating an active fixation helix.

FIG. 5 is a plan view of electrode head assembly having multiple small electrodes disbursed across the distal tip surface of the electrode head assembly.

DETAILED DESCRIPTION OF THE PREFERRED EMBODIMENTS

Figure 6:
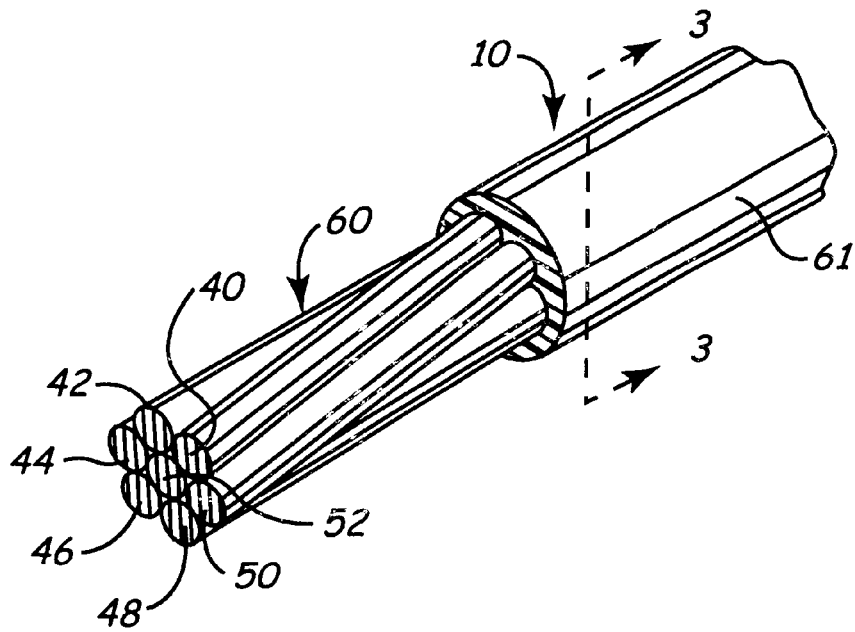
FIG. 6 is a cutaway view through the distal portion of the lead of FIG. 1.

FIG. 1 is a plan view of a lead according to the present invention. The lead is provided with an elongated insulative lead body that carries one or more conductors extending along its length. At the proximal end of the lead body is a connector assembly 12, which includes a connector pin 18 and a connector ring 20. In unipolar leads, connector pin 18 is conducted to a single conductor within lead body 10. In bipolar embodiments, connector ring 20 is coupled to a second conductor within lead body 10. Sealing rings 14 and 16 prevent electrical leakage between connector pin 18 and connector ring 20 in the connector block of a pulse generator in which the lead is inserted.

At the distal end of the lead body is an electrode head assembly 26, from which an electrode 22 protrudes distally. Electrode head assembly 26 includes passive affixation apparatus 24 for affixing the lead to heart tissue. In this embodiment, tine structures are shown as affixation apparatus. Alternatively, metal helix structures may be provided to screw into the heart tissue as discussed in the above cited patent to Mehra.

According to the current invention, the lead body has a diameter of 3 French or less, and is ideally 1 French or less. This design utilizes materials having a Young's modulus of between approximately 25,000 and 660,000 psi. If such materials were used with prior art leads having substantially larger diameter lead bodies, the resulting structures would be too stiff to prevent perforating the heart. (It may be noted that such larger lead designs generally employ materials having a Young's modulus of 600 to 2500 pounds per square inch.) However, according to the current inventive structure, the stiffness of the material has actually been shown to prevent cardiac damage as is discussed further below.

According to one embodiment of the current invention, the lead body includes a polyurethane insulation, Pellethane 2363-55D, having a Young's Modulus of about 25000 psi. The lead body has an Outer Diameter (OD) of 0.042 inches, or about 3.2 French, and an Inner Diameter (ID) of 0.032 inches. The principle discussed above may be utilized to determine bending moment wherein:

$$\text{bending moment} = (\text{Young's modulus}) \times (OD^4 - ID^4)/64.$$

Assuming the conductor is a very flexible, fine wire coil contributing little to the bending moment of the lead, the lead structure has a bending moment of $8 \times 10^{-4}$.

The benefits of the current invention are readily apparent when contrasting the inventive structure to a small-diameter lead manufactured with a softer polyurethane material of the type used in prior art designs. Consider, for example, a 1 French lead made with ethylenetetrafluoroethylene (eTFE, Tefzel) having insulation tubing with a 0.013-inch OD and 0.008-inch ID. Young's modulus for eTFE is about 120000 pounds per square inch (psi). Thus, the bending moment for this tubing is about $4.6 \times 10^{-5}$ lb-in$^2$. When used to insulate a transvenous lead containing a very flexible cabled conductor composed of multiple fine wires (contributing little to the bending moment), the lead will exhibit a "whip-like" movement known to create cardiac damage including numerous coliform vegetations. In contrast, a similar lead structure employing Pellethane 2363-55D as discussed in the foregoing paragraph has a bending moment which is 18 times greater than the lead constructed of eTFE tubing. This increase in flexural stiffness provided by the current invention prevents the whiplike motion and the associated cardiac damage.

To further reduce the risk of damage to the heart due to myocardial perforation, the distal lead surface area used with present larger leads may be utilized. The size of the distal lead surface area is selected such that the pressure exerted against the tissue during lead placement is not greater than 3.6 pounds per-square-inch. Pressure at the distal tip is measured by gripping the lead 10 cm proximal from the distal tip and pushing against a plate with the lead held at a slight angle. The force required at 5% compression (about that seen when implanted in the heart and typically beyond the point where the lead buckles) is divided by the projected area of the distal tip to produce a pressure in pounds per square inch. Therefore, for any given lead stiffness, a very small distal tip increases the risk of perforation. A very large tip avoids that risk but makes the lead very difficult to remove once encapsulated. Leads with distal tips having an area of between 5 to 8 mm$^2$ are generally considered optimum when used with leads having the bending moments described herein.

For example, electrode head assembly 26 is shown to include distal surface 28, the size of which is selected to reduce the surface pressure to no greater than 3.6 pounds per inch during lead placement.

As shown in FIG. 1, lead body can carry an electrode, which is coupled to connector pin 18. In bipolar embodiments, a second electrode would be provided, coupled to a conductor coupled to connector ring 14. The pacing electrode may be, for example, a porous sintered electrode with the capability of eluding a glucocorticosteroid such as dexamethasone sodium phosphate or beclamethasone, similar to those described in U.S. Pat. No. 5,282,844 issued to Stokes et al. and incorporated herein by reference in its entirety, such as shown in FIG. 1.

FIG. 2 illustrates another embodiment of the electrode head assembly incorporating a "ring tip" electrode 30. In this embodiment, the electrode extends around the external periphery of the distal portion of the lead body is utilized. Such an electrode resembles the electrode disclosed in U.S. Pat. No. 5,342,414 issued to Mehra, also incorporated herein by reference in its entirety. As stated above, in a bipolar configuration, a second electrode 32 may be coupled to connector ring 14.

FIG. 3 illustrates electrode head assembly incorporating an electrode 34 that is embedded within the electrode head assembly.

FIG. 4 further illustrate an active fixation helix 36 that may be used both as a fixation device and an electrode. The fixation helix may be permanently positioned outside of the lead body The helix and tissues may be protected from damage during implant by placing the lead and helix within a guiding catheter. The guiding catheter can be designed to rotate the helix for insertion within the myocardium.

In any of the embodiments shown in FIGS. 2 through 4, it will be understood that a second electrode may be added to implement a bipolar arrangement.

FIG. 5 illustrates yet another electrode head assembly having multiple small electrodes 36 and 38 disbursed across the enlarged distal tip surface of the electrode head assembly.

FIG. 6 is a cutaway view through the distal portion of the lead of FIG. 1. In this embodiment, lead body 10 carries conductor 60, which includes seven strands 40 though 52. The strands are covered by the tubing 61 of Pellethane 2363-75D, or an even harder polymer. One or more of the strands may further be individually insulated to provide multiple, electrically isolated conductors for interconnection to different respective electrodes. This conductor design corresponds to that disclosed in U.S. Pat. No. 5,246,014 issued to Williams et al, also incorporated herein by reference in its entirety. Alternatively, un-insulated strands may be employed. Other conductor types may of course also be employed, including 20 strand cables, as described in U.S. Pat. No. 5,845,396 issued to Altman et al, also incorporated herein by reference in its entirety. In still other embodiments, the individual conductors may simply take the form of a fine wire coil wound around the core member of the lead body.

Figure 7:
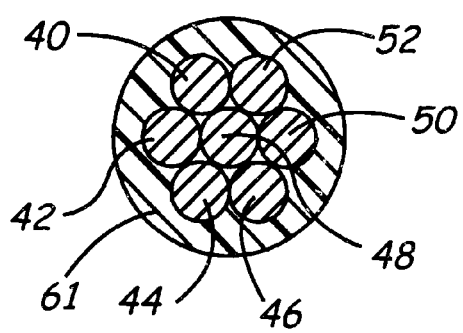
FIG. 7 is a cross-sectional view of the lead body of FIG. 6.

FIG. 7 is a cross-sectional view of the lead body of FIG. 6. This view shows the polyurethane tubing over all of the strands of conductor 60.

Figure 8:
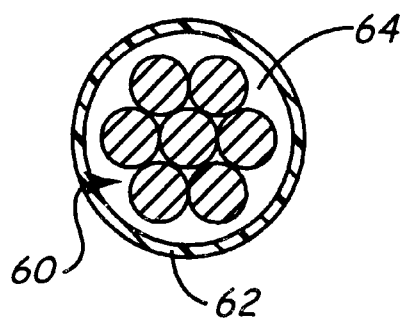
FIG. 8 is a cross-sectional view of a lead of FIG. 6 wherein the lead body is a separately fabricated tube.

FIG. 8 is a cross-sectional view of a lead of FIG. 6 wherein the lead body is a separately fabricated tube 62.

Figure 9:
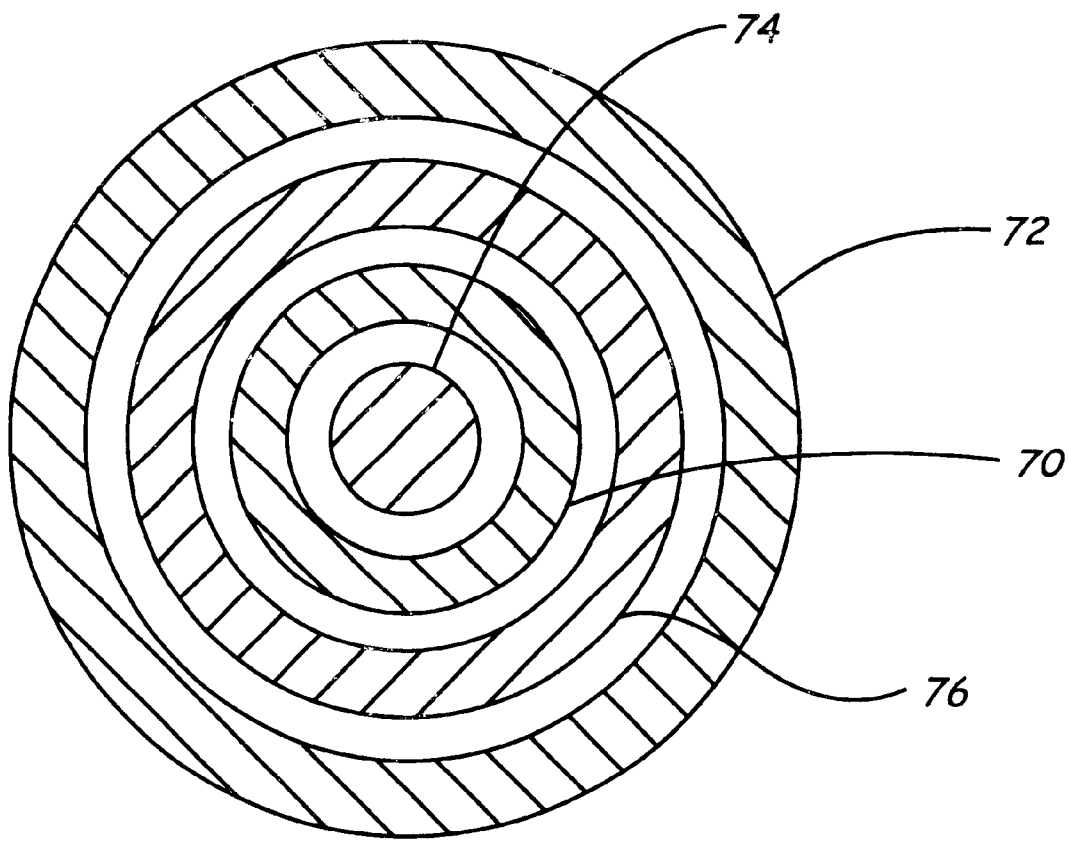
FIG. 9 is a cross-sectional view of yet another embodiment of the present invention using a coaxial bipolar lead structure.

FIG. 9 is a cross-sectional view of yet another embodiment of the present invention using a coaxial bipolar lead structure. This design has an inner insulation tubing 70 and outer insulation tubing 72, both manufactured from Pellethane 2363-55D having a Young's Modulus of about 25,000 psi. The inner insulation tubing may have an inner diameter of about 0.030 inches and an outer diameter of about 0.040 inches. The outer tubing may have an inner diameter of about 0.060 inches and an outer diameter of about 0.070 inches. The bending moments of the two tubes may be added together to obtain the total bending moment for the lead of 0.0241 b-in$^2$. The conductor coils 74 and 76 may be constructed of fine wires designed for flexibility, and thus contributing negligibly to the bending moment. This lead construction preferably has a distal tip that is not reduced in comparison to prior art designs, and which may have an area of about 5.8 mm$^2$.

As yet another example of an embodiment of the current invention, a lead having an outer diameter of 2.9 French (0.038 inches) may be considered. The tubular structure forming the body of the lead has an inner diameter of 0.028 inches. If Pellethane 2363-55D is utilized to form the tubular lead structure, the resulting lead structure has a stiffness of $5.7 \times 10^{-4}$ psi. This lead is therefore thirteen times more stiff than the 1 French lead formed of eTFE tubing of the type discussed above. Animal experiments have shown that, in contrast to small-body leads employing less stiff materials, the current leads do not result in unusual endocardial damage.

According to a similar embodiment, a lead body having the dimensions discussed in the foregoing paragraph may also be manufactured using Pellethane 2363-75D having a Young's modulus of 147,000 psi. This lead has an increased bending moment of $3.4 \times 10^{-3}$, which is seventy-four times greater than a 1 French lead formed of eTFE.

Another embodiment utilizing an even smaller lead having a 2 French (0.026 inch) outer diameter and a 0.016 inch inner diameter may be manufactured of Pellethane 2363-75D, having a Young's modulus of 147,000 psi as discussed above. The resulting lead structure has a bending moment of $9 \times 10^{-4}$ pounds-in$^2$. As in the previous examples, the current example assumes that any conductor carried by the lead does not add to the bending moment of the lead body, which is a fair assumption in most embodiments.

An even smaller embodiment utilizing a polymer having a Young's modulus of 660,000 psi may be manufactured to create a lead structure having an outer diameter of 1.2 French (0.016 inches) and an inner diameter of 0.007 inches. The bending moment of the lead is approximately $6.5 \times 10^{-4}$ psi. This is 12% higher than the bending moment of the 2.9 French embodiment discussed above which was shown to have acceptable performance. An example of such a polymer is hydrolytically stable and biocompatible Genymere polyimide from Virginia Power Nuclear Services Company.

In any of the above examples, a material that has a much larger Young's modulus than is typically used in lead technology is used to provide a structure that minimizes damage to cardiac tissue due to whip-like motions caused by the movement of the heart while beating.

The above-described relationships are illustrated in Table 1. This table illustrates the elastic modulus required to keep the bending moment of a tube constant at 0.001 lb-in$^2$ as a function of tube diameter for a constant wall thickness of 0.005 inches. The Polymers that correspond to various ones of the modulus values are also shown.

TABLE 1

Elastic Modulus Required to Keep Bending Moment Constant at $1 \times 10^{-3}$ in-lb$^2$ as a Function of Tubing Diameter with 0.005 inch thick walls

| Tubing OD (in.) | Modulus (psi) | Polymer |
|---|---|---|
| 0.01 | 640000 | |
| 0.018 | 63441 | Genymere Polyimide |
| 0.02 | 42666 | |
| 0.027 | 14288 | Pellethane 2363-75D |
| 0.03 | 98461 | |
| 0.04 | 36571 | Pellethane 2363-55D |
| 0.05 | 17344 | Pellethane 2363-55D |
| 0.06 | 9538 | |
| 0.07 | 5791 | |
| 0.08 | 3775 | Pellethane 2363-80A |

Many modifications and variations of the present invention are possible in light of the above teachings. For example, the lead body could carry one or more biological sensors. It is therefore to be understood that, within the scope of the appended claims, the invention may be practiced otherwise than as specifically described.

What is claimed is:

1. A medical electrical lead, comprising:
   a lead body having an outer diameter of no greater than 3 French, the lead body being formed of a biocompatible material having a Young's modulus of at least 25,000 pounds per square inch;
   a conductor carried by the lead body; and
   an electrode electrically coupled to a distal end of the conductor.

2. The medical electrical lead of claim 1, wherein the biocompatible material is Pellethane 2363-75D.

3. The medical electrical lead of claim 1, wherein the biocompatible material is a polyurethane.

4. The medical electrical lead of claim 1, wherein the biocompatible material is a polyimide.

5. The medical electrical lead of claim 1 or claim 2 or claim 3, wherein the lead body has an outer diameter of nominally 1 French.

6. The medical electrical lead of claim 1 or claim 2 or claim 3, wherein a distal end of the lead body has a surface area of approximately 6 mm$^2$ to carry the electrode.

7. The medical electrical lead of claim 6, wherein the enlarged surface area has a surface area adapted to exert no greater than 3.6 pounds per square inch on contacting surfaces during placement of the medical electrical lead.

8. The medical electrical lead of claim 1 or claim 2 or claim 3, and further including an affixation device coupled to a distal end of the lead body.

9. The medical electrical lead of claim 1 or claim 2 or claim 3, wherein the biocompatible material lead body is extruded over the conductor.

10. The medical electrical lead of claim 1 or claim 2 or claim 3, wherein the biocompatible material lead body is a separately formed tube surrounding the conductor.

* * * * *

UNITED STATES PATENT AND TRADEMARK OFFICE
Certificate

Patent No. 6,366,819 B1                                                                                                                               Patented: April 2, 2002

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Kenneth B. Stokes, Anoka, MN (US); Michael J. Ebert, Fridley, MN (US); and Kenneth R. Brennen, Zimmerman, MN (US).

Signed and Sealed this Twelfth Day of October 2010.

CARL H. LAYNO
                                                                              *Supervisory Patent Examiner*
                                                                                        Art Unit 3766
                                                                            Technology Center 3700